United States Patent
Pohan

(10) Patent No.: US 8,059,786 B2
(45) Date of Patent: Nov. 15, 2011

(54) SCATTERED RADIATION COLLIMATOR, RADIATION DETECTOR AND RADIATION DETECTION DEVICE

(75) Inventor: Claus Pohan, Baiersdorf (DE)

(73) Assignee: Siemens Aktiengellschaft, Munich (DE)

( * ) Notice: Subject to any disclaimer, the term of this patent is extended or adjusted under 35 U.S.C. 154(b) by 100 days.

(21) Appl. No.: 12/458,254

(22) Filed: Jul. 7, 2009

(65) Prior Publication Data
US 2010/0014633 A1 Jan. 21, 2010

(30) Foreign Application Priority Data

Jul. 8, 2008 (DE) .................... 10 2008 032 137

(51) Int. Cl.
*G21K 1/10* (2006.01)
(52) U.S. Cl. ........................................ 378/154; 378/147
(58) Field of Classification Search .................... 378/19, 378/147, 154
See application file for complete search history.

(56) References Cited

U.S. PATENT DOCUMENTS

| | | | |
|---|---|---|---|
| 4,845,731 A * | 7/1989 | Vidmar et al. ................... | 378/98 |
| 5,444,752 A * | 8/1995 | Dobbs et al. .................... | 378/19 |
| 5,991,357 A * | 11/1999 | Marcovici et al. ............... | 378/19 |
| 6,055,296 A * | 4/2000 | Ferlic et al. ..................... | 378/154 |
| 6,587,538 B2 * | 7/2003 | Igarashi et al. .................. | 378/19 |
| 7,257,195 B2 | 8/2007 | Freund et al. | |
| 7,356,124 B2 | 4/2008 | Freund et al. | |
| 2005/0135562 A1* | 6/2005 | Freund et al. .................. | 378/147 |
| 2006/0067479 A1* | 3/2006 | Freund et al. .................. | 378/149 |
| 2006/0233298 A1 | 10/2006 | Ryuhachiro | |
| 2006/0291617 A1* | 12/2006 | Freund et al. .................... | 378/19 |

FOREIGN PATENT DOCUMENTS

| DE | 10361510 A1 | 7/2005 |
|---|---|---|
| DE | 102005028411 A1 | 12/2006 |

* cited by examiner

*Primary Examiner* — Edward Glick
*Assistant Examiner* — Thomas R Artman
(74) *Attorney, Agent, or Firm* — Harness, Dickey & Pierce, P.L.C.

(57) ABSTRACT

A scattered radiation collimator is disclosed for radiological radiation. In at least one embodiment, the scattered radiation collimator includes a multiplicity of absorber elements connected one behind the other in a collimation direction and at least two plate-like holding elements which are arranged substantially parallel with respect to one another and have absorber element holders for holding the absorber elements. In order to avoid erroneous positioning when transverse forces are acting, it is proposed in at least one embodiment, to connect the holding elements to each other by cross beams running along the end face of the absorber elements.

19 Claims, 3 Drawing Sheets

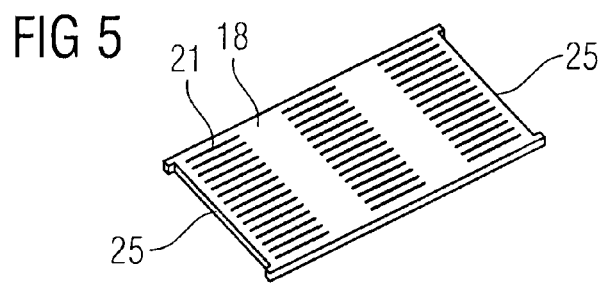
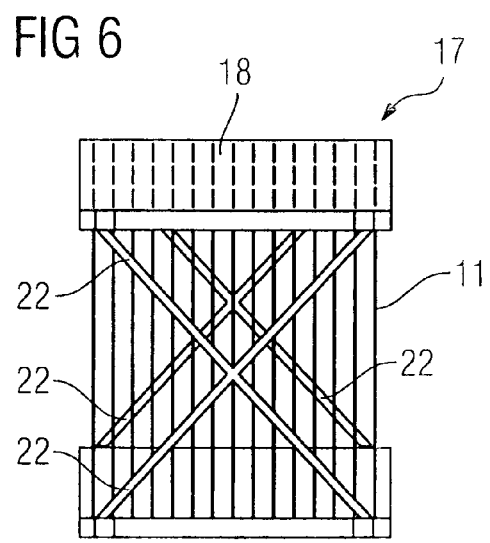
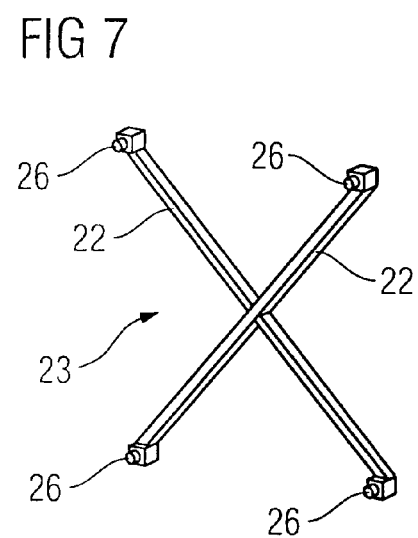
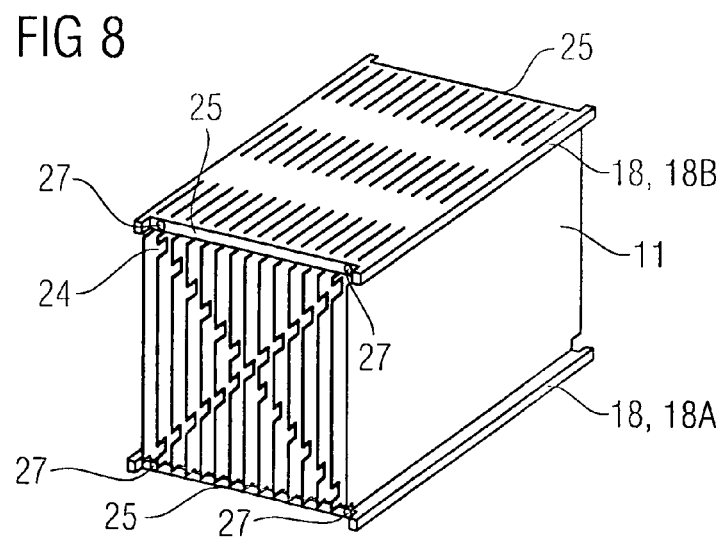

US 8,059,786 B2

SCATTERED RADIATION COLLIMATOR, RADIATION DETECTOR AND RADIATION DETECTION DEVICE

PRIORITY STATEMENT

The present application hereby claims priority under 35 U.S.C. §119 on German patent application number DE 10 2008 032 137.0 filed Jul. 8, 2008, the entire contents of which are hereby incorporated herein by reference.

FIELD

At least one embodiment of the invention generally relates to a scattered radiation collimator for radiological radiation.

BACKGROUND

It is well-known that scattered radiation impairs the image quality, particularly in the case of imaging tomography equipment such as, for example, X-ray computed tomography devices. It is for this reason that such tomography devices generally comprise radiation detectors which have so-called scattered radiation collimators arranged upstream of them in order to reduce the scattered radiation.

Known scattered radiation collimators comprise, for example, absorber elements which are arranged next to one another in a collimation direction and are aligned in one direction with respect to their longitudinal extent, with absorber surfaces of the absorber elements running substantially perpendicular to the respective collimation direction. This makes it possible to suppress scattered radiation occurring in the collimation direction, which scattered radiation is caused, for example, by the radiation being scattered on an object to be examined.

For example, DE 103 61 510 A1 discloses a collimator for a computed tomography scanner, which has a collimator lower part and a collimator upper part as holders for collimator plates. The collimator lower part comprises groove-like recesses on the end face for collimator plates in addition to lug receptacles on the bottom side. The collimator upper part is screwed to the collimator lower part in order to form the collimator.

US 2006/0233298 A1 describes a collimator with an upper and a lower annular-segment-like holding element. The holding elements have grooves for collimator sheets. The annular-segment-like holding elements are connected to each other by means of side parts.

The absorber elements of known scattered radiation collimators are generally comparatively thin and delicate. As a result of this, the absorber elements as such have low mechanical stability and are therefore not very dimensionally stable. Particularly in the case of acting forces, such as, for example, centrifugal forces acting on the absorber elements and transverse forces acting across the connection axis X-ray tube/X-ray detector during the operation of an X-ray computed tomography device, and other mechanical effects, the absorber elements can be deformed to such an extent that artifacts occur as a result of this. By way of example, this can be the case if the—or individual—absorber elements are deformed or displaced to the extent that detector elements of the radiation detector are shadowed.

In order to avoid deformations and temporary displacements or erroneous positioning, it is common practice, for example, to adhesively bond the absorber elements using suitably designed holding lugs which extend into the intermediate spaces between the absorber elements. Aside from the comparatively high production complexity, this additionally poses the problem of irreversible erroneous positioning of the absorber elements possibly being caused by adhesive bond contraction during the curing of an adhesive bond used for the adhesive bonding.

DE 10 2005 028 411 A1 describes a collimator for a beam detector which has a number of collimator sheets arranged next to one another and between which respectively at least one support element is arranged for stiffening the collimator, which support element is composed of an X-ray transparent material and supports the collimator sheets from the side.

SUMMARY

In at least one embodiment of the invention, at least one of the disadvantages according to the prior art is reduced or even removed. In particular, a scattered radiation collimator is intended to be provided, in which the absorber elements, using simple design measures, can be held in a dimensionally stable manner. From the same considerations, a radiation detector and a radiation detection device are also intended to be specified.

A first aspect of at least one embodiment of the invention relates to a scattered radiation collimator for radiological radiation. The scattered radiation collimator comprises a multiplicity of absorber elements connected one behind the other in a collimation direction and at least two plate-like holding elements which are arranged substantially parallel with respect to one another. The holding elements can, for example, comprise a paired base and cover plate. The base and cover plates can be arranged on transverse and/or longitudinal edges lying opposite one another. In this case, a distance between the base and cover plate can basically correspond to the longitudinal or transverse extent of the absorber elements. It is also possible for the distance between the base and cover plate to be smaller than the longitudinal or transverse extent of the absorber elements.

The holding elements have absorber element holders, for example in the form of slits or the like, to hold the absorber elements. By way of example, the absorber elements can be held on the transverse or longitudinal edges by way of the absorber element holders.

According to at least one embodiment of the invention, the plate-like holding elements are connected to each other by cross beams, the cross beams running along the end face with respect to the longitudinal extent and/or with respect to the transverse extent of the absorber elements.

As a result of the concept of the cross beams according to at least one embodiment of the invention, the holding elements can be made stiffer relative to each other in a simple but nevertheless effective manner, so that a relative displacement, deformation, or erroneous positioning of the holding elements caused by mechanical influences, such as, for example, forces acting as a result of the rotation and the like, are avoided as far as possible. As a result, a set position of the absorber elements fixed by the holding elements can substantially be maintained even when forces act, so that artifacts caused by deformation and the like of the absorber elements can be avoided.

Apart from that, adhesively bonding the absorber elements using holding and supporting elements engaging between the absorber elements can be dispensed with as a result of the stabilizing effect of the cross beams. To this extent, the initially mentioned problem of erroneous positioning as a result of adhesive bond contraction can easily be circumvented.

By way of example, the absorber element holders can be slits, recesses, depressions, in particular grooves or channels, and/or projections, etc. Such absorber element holders can be produced comparatively easily, particularly in the case of plate-like holding elements. By way of example, they make it possible to hold the absorber elements on the edge on transverse and/or longitudinal sides in a predetermined set alignment. Possible set alignments of the absorber elements, which can, for example, be collimator sheets, are: a parallel alignment of the collimator sheets or a confocal alignment of the collimator sheets.

So that particularly secure holding of the absorber elements by the absorber element holders can be ensured, it is possible for the absorber elements to have notches on the edge side and/or protruding lugs which engage into the absorber element holders. Lugs or notches of the type mentioned above can be provided on one or more sides of the absorber elements.

With regard to a particularly high mechanical stability of the scattered radiation collimator with respect to external effects, it is advantageous if in each case at least one cross beam is arranged or attached to at least two end faces lying opposite one another. A particularly high stability can be achieved if two crossing cross beams are attached to at least one of the end faces lying opposite one another.

In the case of two crossing cross beams, the crossing cross beams can form an integrally-formed cross brace in order to simplify production and mounting.

In order to ensure that the scattered radiation collimators can be adjoined from all sides, the cross beams on the end faces can at least partially be lowered into the absorber elements. To this end, the absorber elements can have recesses corresponding to the profile of the cross beams on the end face. The cross beams can be lowered into a channel-like incision formed by the recesses.

It is advantageous if the recesses are formed such that mechanical contact between the absorber elements and the cross beams is avoided. This makes it possible to avoid erroneous positioning of the absorber elements possibly caused by mechanical contact. In the case of tightly fitting recesses, such erroneous positioning can be caused, for example, as a result of production tolerances of the recesses and cross beams. It is also possible for different thermal expansion coefficients of the cross beams and absorber elements to lead to stresses and hence possibly lead to deformations and erroneous positioning of the absorber elements.

In order to keep an impairment of measurement results caused by the scattered radiation collimator with cross beams as low as possible, the holding elements and the cross beams can be suitably arranged and designed. In this case, it is advantageous if an attenuation of the radiation in the radiation transit direction, caused by a combination of holding elements and cross beams, in the region of the cross beams, is approximately equal to an attenuation of the radiation in the radiation transit direction, caused by the holding elements only, in a cross-beam-free region.

Here, the term "radiation transit direction" is intended to be understood to mean that direction in which the radiation is intended to pass through when used in the intended manner. It is understood that the absorber elements also effect attenuation in the radiation transit direction as a result of their thickness. However, this should not change any aspect of the present definition of the radiation transit direction. Under closer scrutiny, the radiation transit direction is fixed by that direction in which the radiation is intended to pass through between the absorber elements without hindrance. In the case of confocally aligned absorber elements, the radiation transit direction is a local variable which depends on the confocal alignment of the absorber elements.

To the extent that the demands with respect to precision make it necessary and the production complexity is justified, the cross beams can, in those regions in which said beams are lowered in the recesses, be designed such that their degree of absorption substantially corresponds to that of the absorber elements.

A particularly stable embodiment which can be produced easily can be achieved by the cross beams running substantially diagonally on the end face. In this case, substantially diagonally is intended to mean that the cross beams run from one corner of a holding element, transversely across the end face, and to a corner of another holding element. The phrasing "substantially diagonally" is also intended to include the case where the clear distance between two holding elements is smaller than the transverse or longitudinal extent of the absorber elements.

In order to attach the cross beams to the holding elements, substantially arbitrary attachment device(s) or attachment methods can be considered which depend, inter alia, on the material and geometry of the holding elements and cross beams. In particular, the cross beams and the holding elements can be connected to one another by means of bolts or pins and corresponding bores, by means of screws and/or by means of an adhesive connection.

A second aspect of at least one embodiment of the invention relates to a radiation detector comprising a detection unit for detecting radiological radiation and a scattered radiation collimator according to the first aspect of the invention arranged upstream of the detection unit.

A third aspect of at least one embodiment of the invention relates to a radiation detection device, in particular an X-ray computed tomography device, comprising a radiation detector according the second aspect of at least one embodiment of the invention.

Advantages and advantageous effects of the second and third aspect of at least one embodiment of the invention result directly from the advantages and advantageous effects of the first aspect of at least one embodiment of the invention.

BRIEF DESCRIPTION OF THE DRAWINGS

In the following text, example embodiments of the invention will be explained in more detail on the basis of figures, in which:

FIG. 5 shows a holding element of the scattered radiation collimator;

FIG. 6 shows a perspective frontal view of the scattered radiation collimator;

FIG. 7 shows a cross brace of the scattered radiation collimator; and

FIG. 8 shows the scattered radiation collimator without a cross brace.

DETAILED DESCRIPTION OF THE EXAMPLE EMBODIMENTS

Figure 1:
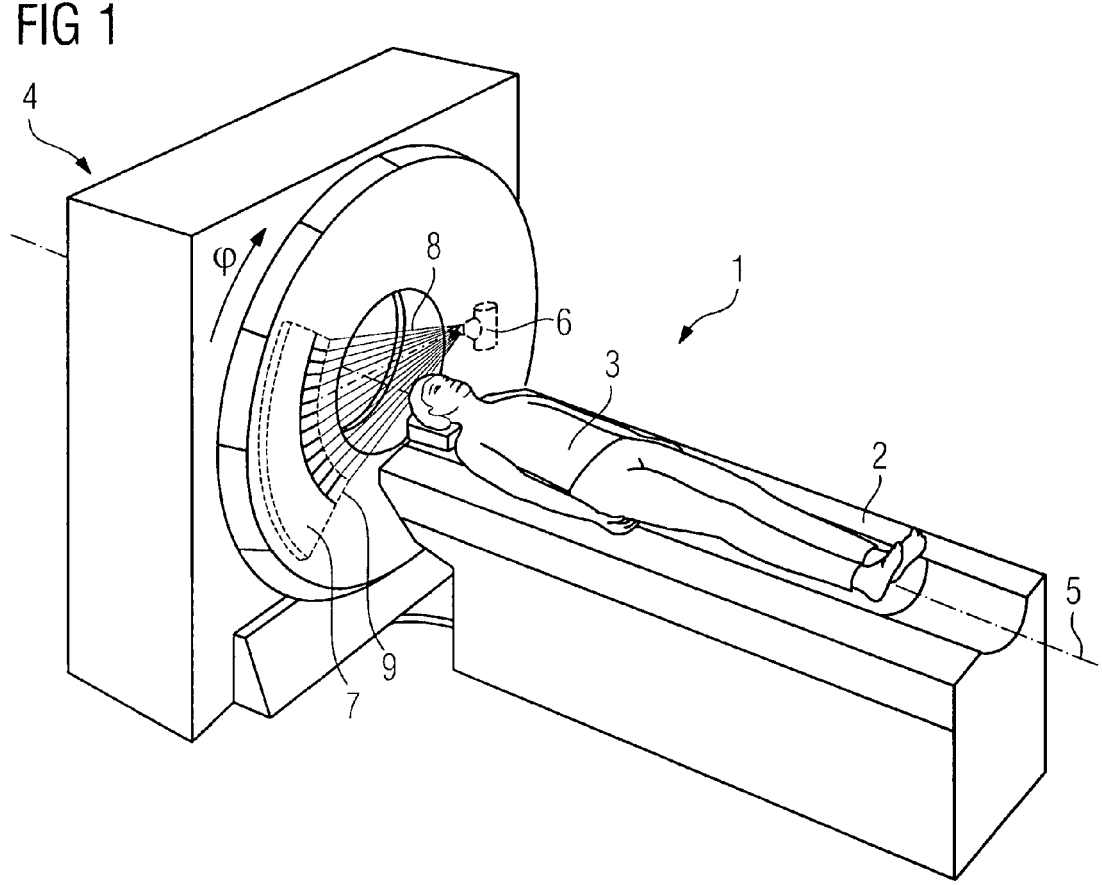
FIG. 1 schematically shows an X-ray computed tomography device as an example of a radiation detection device according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, equivalent or functionally equivalent elements are always designated by the same reference symbol. The illustrations in the figures are schematic and not to scale, and the scale can vary between figures. Without loss of generality, the invention will be described below on the basis of X-ray computed tomography.

FIG. 1 schematically shows an X-ray computed tomography device 1, comprising a patient support table 2 for supporting a patient 3 to be examined. The X-ray computed tomography device 1 furthermore comprises a gantry 4 with a tube/detector system rotatably mounted about a system axis 5 in the azimuthal direction $\phi$. The tube/detector system in turn comprises an X-ray tube 6 and an X-ray detector 7 arranged opposite thereto.

During operation of the X-ray computed tomography device 1, X-ray radiation 8 is emitted by the X-ray tube 6 in the direction of the X-ray detector 7 and is detected by means of the X-ray detector 7. The X-ray detector 7 has a number of radiation detector modules 9 to detect the X-ray radiation 8.

Scattered radiation 10 is generated when the X-ray radiation 8 passes through the body of the patient 3 and during the interaction processes occurring thereby. The scattered radiation 10 leads to a reduced image quality in the tomographic illustrations or images generated from the recorded data of the X-ray computed tomography device 1.

Figure 2:
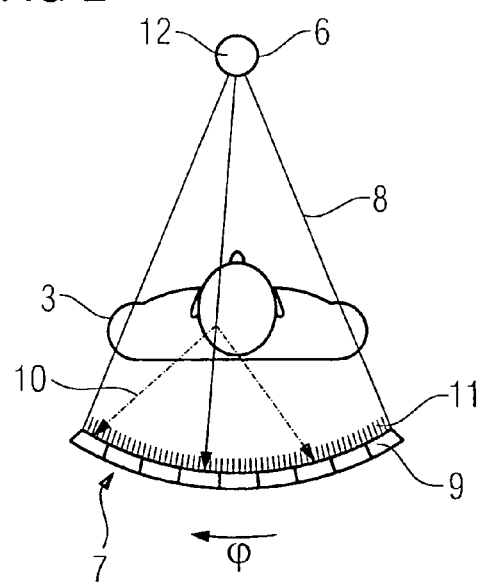
FIG. 2 shows the occurrence of scattered radiation in a schematic illustration.

The occurrence of scattered radiation 10 is illustrated schematically for the azimuthal direction $\phi$ in FIG. 2. Analogous results hold for the occurrence of scattered radiation in the direction of the system axis 5; this is not described in any more detail. Reference is made to the fact that the following explanations also hold for scattered radiation collimators whose collimation direction corresponds to the direction of the system axis.

The radiation detector modules 9 generally comprise one or more, e.g. modular, scattered radiation collimators with a multiplicity of absorber elements 11 to suppress the azimuthal scattered radiation 10. In accordance with the confocal beam geometry in the present case, the absorber elements 11 are aligned confocally with a focus 12 of the X-ray tube 6.

The absorber elements 11 are arranged one behind the other in the azimuthal direction $\phi$, which in the present example corresponds to the collimation direction. In the present case, a radiation transit direction 13 corresponds to the radial direction with respect the focus 12.

Inasmuch as there is an intension of providing further absorber elements for suppressing scattered radiation in the direction of the system axis 5, said elements are arranged one behind the other in the direction of the system axis 5 and are preferably arranged confocally with respect to the focus 12.

The absorber elements 11 are generally delicate, fine small plates or sheets with a comparatively small thickness. As a result of this, the absorber elements 11 do not have a particularly high mechanical stability.

However, relatively large acceleration forces act on the absorber elements 11 in the case of a circular or helical scan of the patient 3, in which the tube/detector system is rotated about the system axis 5. This makes it possible for the absorber elements 11 to be deformed and displaced temporarily. This leads to erroneous positioning of the absorber elements 11 which in turn can lead to artifacts in the images.

Forces which act across the focus 12/radiation detector module 9 connection axis can in particular cause displacements and erroneous positioning of the absorber elements 11. Such forces are, in a simplified manner, referred to as transverse forces in the following text.

As already mentioned initially, it is common practice to insert holding lugs into the intermediate spaces between the absorber elements and to adhesively bond said lugs to the absorber elements by means of an adhesive bond to avoid displacements and deformations caused by transverse forces. However, contraction processes of the adhesive bond inevitably lead to the absorber elements being positioned erroneously or being deformed. In particular, such production-dependent, artifact-inducing erroneous positioning and deformations can be avoided using the solution according to the invention, as will be explained in more detail in the following text.

Figure 3:
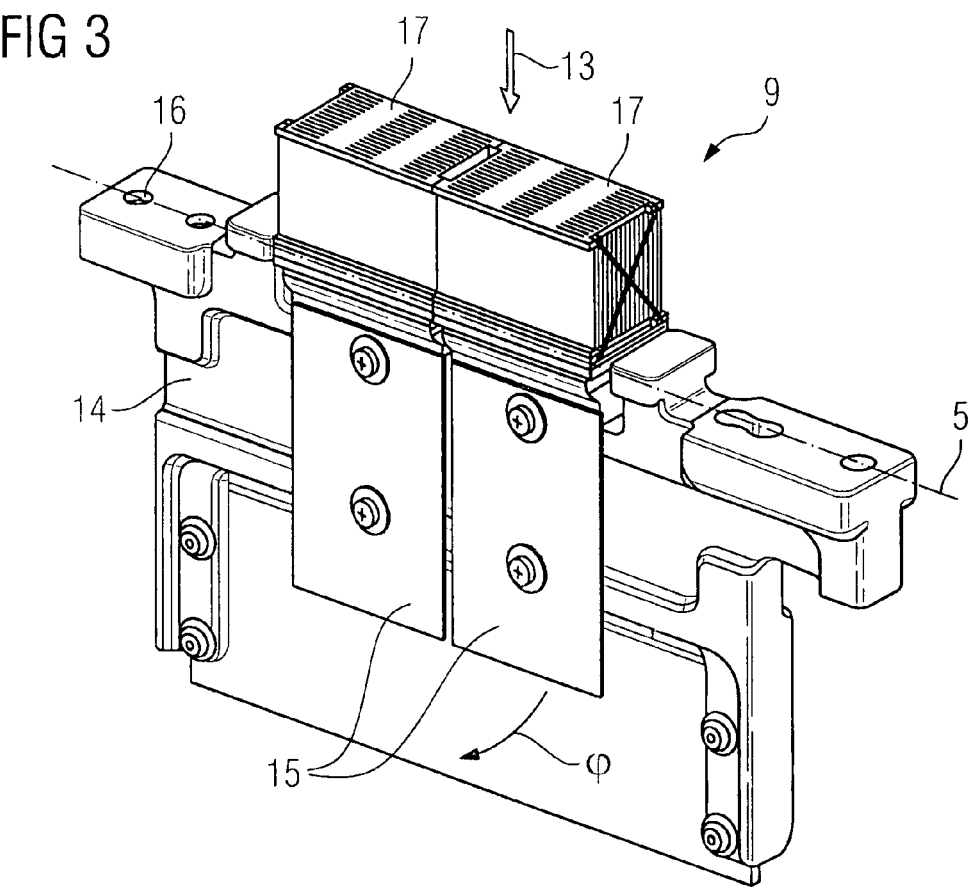
FIG. 3 shows a radiation detector module with scattered radiation collimators.

FIG. 3 shows the radiation detector module 9 illustrated schematically in FIG. 1 in more detail.

The radiation detector module 9 has two detection units 15 mounted on a support 14 in the direction of the system axis. In general, an arbitrary number of detection units 15 can be arranged on a correspondingly designed support or on other attachment apparatuses. In this respect, the illustrated refinement with two detection units 15 mounted on the support 14 should not be seen as limiting.

In the present case, the support 14 has through-holes 16 for attaching a plurality of supports 14 on a holding frame of the X-ray detector 7 not shown in any more detail, for example by way of screws. FIG. 1 shows that a plurality of radiation detector modules 9 or supports 14 are mounted one behind the other in the azimuthal direction φ on the holding frame.

In the embodiment of FIG. 3, each detection unit 15 respectively has a scattered radiation collimator 17 connected upstream thereof, the scattered radiation collimators 17 being arranged next to one another like tiles in accordance with the detection units 15. However, it is also possible that, deviating from the illustration of FIG. 3, only one scattered radiation collimator is provided which spans both detection units 15.

The scattered radiation collimators 17 can be adhesively bonded to the detection units 15 or can be attached in any other suitable manner.

Figure 4:
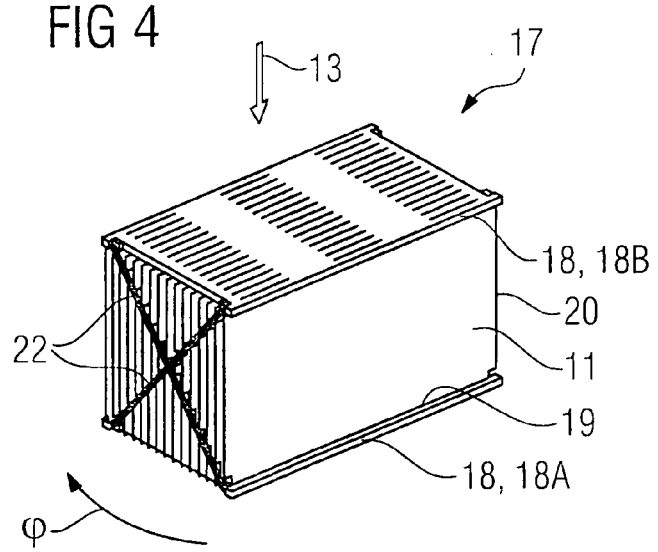
FIG. 4 shows a perspective side view of a scattered radiation collimator designed according to an embodiment of the invention.

FIG. 4 shows one of the scattered radiation collimators 17 in detail. As mentioned previously, the scattered radiation collimator 17 comprises a multiplicity of absorber elements 11 connected one behind the other in the collimation direction, i.e. the azimuthal direction 9. The scattered radiation collimator 17 comprises two plate-like holding elements 18 which are arranged substantially parallel with respect to one another in order to hold the absorber elements 11. For the purposes of simplification, in the following text, one of the holding elements 18 is referred to as the base plate 18A and the other is referred to as the cover plate 18B. In the present example embodiment, the holding elements 18 are arranged on longitudinal edges 19 of the absorber elements 11. However, additionally or optionally, it is also possible for one or more holding elements to be arranged on transverse edges 20 of the absorber elements 11.

Each holding element 18 comprises absorber element holders 21 for holding the absorber elements 11, as can be seen in more detail in FIG. 5, which shows an individual holding element 18. In the present example, the absorber element holders 21 are designed as slits, into which lugs engage which are formed on the longitudinal edges 19 of the absorber elements 11 and are not illustrated in any more detail. The absorber element holders 21 hold the absorber elements 11 according to a respectively desired set position and bearing.

As an alternative thereto, or additionally, it is also possible for the absorber element holders 21 to be designed in the form of recesses and/or depressions, in particular grooves or channels. In this case, the channels or depressions can for example be designed such that the absorber elements 11 can be inserted on the edge side with longitudinal 29 or transverse 20 edges and can be held therewith. Differently designed absorber element holders are feasible, such as, for example, projections in the form of pins, rails, or the like, arranged in pairs.

FIG. 4 shows that the holding elements 18, that is to say the base plate 18A and the cover plate 18B, are connected to one another by means of cross beams 22. The cross beams 22 run on the end face, that is to say on the end face of the scattered radiation collimator 17 spanned by the transverse edges 20, with respect to the longitudinal extent of the absorber elements 11.

Only one end face is visible in the perspective side view of FIG. 4. However, in an analogous manner, cross beams 22 run on the end face which is not visible and faces away in the illustration. The perspective frontal view of FIG. 6 shows this.

The cross beams 22 attached according to the invention can, in a simple design and production-technical manner, counteract displacement, deformation, and erroneous positioning of the absorber elements 11 caused in particular by transverse forces. The concept of the cross beams 22 according to an embodiment of the invention accordingly makes reliable and stable positioning of the absorber elements 11 possible.

The holding elements 18 and cross beams 22 can for example be produced relatively simply, and therefore economically, and moreover with a very high precision, by way of an injection molding method.

In the present example, respectively two crossing cross beams 22 are arranged on the end faces lying opposite to one another. The cross beams 22 run diagonally on the end faces. The diagonal profile of the cross beams 22 is particularly advantageous from the point of view of stability. Furthermore, such a profile makes comparatively uncomplicated attachment possibilities of the cross beams 22 on the holding elements 18 possible; this will be explained further below in more detail.

It is feasible, and convenient within the scope of embodiments of the invention, if only one cross beam 22 is present on one or all end faces. In any case, for reasons of stability, at least two cross beams 22 should be present in an opposing, crossing arrangement.

Furthermore, it is within the scope of embodiments of the invention if in each case non-crossing cross beams are present on one or on both end faces. Such cross beams could, for example, run substantially parallel to one another and connect the holding elements 18 to each other.

In order to avoid displacements, deformations, and erroneous positioning when transverse forces are acting, further arrangements and designs of cross beams 22 are feasible. For example, it would also be feasible for holding elements 18 to be attached to the end faces and the cross beams 22 to run transversely over the longitudinal edges 19.

Returning to the refinement shown with reference to the figures, two crossing cross beams 22 are arranged on each end face. In this case, the cross beams 22 on an end face can be designed as bracing elements which are independent of one another. Alternatively, it is also possible for the cross beams 22 to be combined as one unit on a respective end face. This is shown in FIG. 7, where the cross beams 22 are connected to each other and in this manner form an integrally-formed cross brace 23. Such cross braces 23 can reduce the mounting complexity of the cross beams 22 on the holding elements 18.

So that the scattered radiation collimators 17 can be arranged adjacently to one another on the end faces whilst avoiding comparatively large gaps, it is particularly advantageous if the cross beams 22 are at least in part lowered into the absorber elements 11 on the end face. To this end, the absorber elements 11 can have recesses 24 corresponding to the—in this case diagonal—profile of the cross beams 22. This can be seen in FIG. 8 which shows the scattered radiation collimator 17 without cross beams 22.

The recesses 24 are designed such that the cross beams 22 can at least in part be lowered into said recesses. The depth of the recesses 24, that is to say the degree to which the cross beams 22 can be lowered into the recesses 24, can be selected according to the desired or permissible projection of the cross beams 22 beyond the transverse edges 20 of the absorber elements 11.

The recesses 24 are preferably designed such that mechanical contact between the absorber elements 11 and the cross beams is avoided. By way of example, the recesses 24 can be designed to be so large that, taking into account the production tolerances of recesses 24 and cross beams 22, a gap remains between the cross beams 22 and recesses 24, even after the cross beams 22 have been mounted. Otherwise, it could be possible for erroneous positioning of the absorber elements 11, caused by mechanical contact, to occur for example during the mounting of the cross beams 22, that is to say when the cross beams 22 are inserted into the recesses 24. The shape of the recesses 24 can basically be selected freely under the proviso that the cross beams 2 can be lowered to the desired extent, preferably whilst avoiding mechanical contact with the absorber elements 11. By way of example, it can be possible to select shapes which can be produced particularly easily and cost-effectively, such as, for example, rectangular or circular shapes.

The holding elements 18 and the cross beams 22 cause an—albeit comparatively small—absorption of the X-ray radiation 8 in the radiation transit direction 13. So that the scattered radiation collimator 17 has an absorption profile which is as even as possible in the radiation transit direction 13, it is advantageous if the holding elements 18 and the cross beams 22 are arranged and designed such that an attenuation of the X-ray radiation 8 in the radiation transit direction 13, caused by the holding elements 18 and the cross beams 22, in the region of the cross beams 22, is approximately equal to an attenuation of the X-ray radiation 8 in the radiation transit direction 13, caused by the holding elements 18 only, in a cross-beam-free region. A corresponding refinement in the present example embodiment is clear from a combined view of FIGS. 5, 7 and 8. FIGS. 5 and 8 show that the holding elements 18 respectively have an offset 25 on the respective end face in that region in which the cross beams 22 come to rest. The offset 25 is selected such that the holding elements 18 and the cross beams 22 do not overlap when viewed in the radiation transit direction 13. So that a uniform absorption profile can be ensured, the cross beams 22 of the respective end faces are designed such that their absorption—when viewed in the radiation transit direction 13—locally substantially equals the local absorption of the two holding elements 18 outside of the region of the cross beams 22. In order to achieve a substantially equal absorption, it is possible to select cross beams 22 with a correspondingly dimensioned cross section and/or with a suitable material composition.

With respect to a uniform absorption profile of the scattered radiation collimator 17, attachment elements for attaching the cross beams 22 on the holding elements 18 should also, if provided, be designed appropriately.

In the present refinement, in particular taking account of FIGS. 7 and 8, the cross beams 22 have protruding pins 26 or bolts which are inserted or pressed into corresponding bores 27 of the holding elements 18 in order to mount the cross beams 22 on the holding elements 18. As long as at least the pins 26 are produced from the same material as the holding elements 18, it is also possible to avoid a discontinuous change of the absorption property in the region of the attachment elements.

It is within the scope of an embodiment of the invention for the bores 27 and the pins 26 to be interchanged, or for the cross beams 22 and the holding elements 18 to respectively have bores 27 into which a pin is inserted in order to mount the cross beams 22. Within the scope of an embodiment of the invention, it is also possible for other or additional attachment possibilities to be used. For example, an adhesive connection between the cross beams 22 and the holding elements 18 is possible.

The concept according to an embodiment of the invention allows the provision of a scattered radiation collimator 17 which makes particularly dimensionally stable holding of the absorber elements 11 possible, in particular when transverse forces are acting. Furthermore, the scattered radiation collimator 17 according to the invention can be produced in a particularly simple and therefore cost-effective manner. Overall, particularly on the basis of the exemplary embodiments explained with reference to the figures, it is clear that the object on which an embodiment of the invention is based is achieved.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A scattered radiation collimator for radiological radiation, comprising:
   a multiplicity of absorber elements connected one behind another in a collimation direction; and
   at least two plate holding elements, arranged substantially parallel with respect to one another and including absorber element holders for holding the absorber elements, the at least two plate holding elements being connected to each other by cross beams running along an end face with respect to each of the absorber elements.

2. The scattered radiation collimator as claimed in claim 1, wherein the absorber element holders include at least one of slits, recesses, depressions, and projections.

3. The scattered radiation collimator as claimed in claim 2, wherein the absorber elements include at least one of notches on an edge side and protruding lugs which engage into the absorber element holders.

4. The scattered radiation collimator as claimed in claim 2, wherein the absorber element holders include grooves or channels.

5. A radiation detector, comprising:
   at least one detection unit configured to detect radiological radiation; and
   the scattered radiation collimator as claimed in claim 2, arranged upstream of the at least one detection unit.

6. A radiation detection device, comprising the radiation detector as claimed in claim 5.

7. The radiation detection device as claimed in claim 6, wherein the radiation detector is an X-ray computed tomography device.

8. The scattered radiation collimator as claimed in claim 1, wherein at least one cross beam is arranged on at least two opposite end faces.

9. The scattered radiation collimator as claimed in claim 8, wherein the at least one cross beam includes at least two cross beams, the at least two cross beams forming an integrally-formed cross brace.

10. The scattered radiation collimator as claimed in claim 8, wherein at least two crossing cross beams are, in each case, arranged on at least two opposite end faces.

11. The scattered radiation collimator as claimed in claim 1, wherein the cross beams run substantially diagonally on the end face.

12. The scattered radiation collimator as claimed in claim 1, wherein at least one of bolts, pins, screws and adhesive connect the cross beams and the at least two plate.

13. The scattered radiation collimator as claimed in claim 1, wherein the absorber elements are aligned confocally with respect to a focus.

14. A radiation detector, comprising:
   at least one detection unit configured to detect radiological radiation; and
   the scattered radiation collimator as claimed in claim 1, arranged upstream of the at least one detection unit.

15. A radiation detection device, comprising the radiation detector as claimed in claim 14.

16. The radiation detection device as claimed in claim 15, wherein the radiation detector is an X-ray computed tomography device.

17. A scattered radiation collimator comprising:
   a multiplicity of absorber elements connected one behind another in a collimation direction; and
   at least two plate holding elements, arranged substantially parallel with respect to one another and including absorber element holders for holding the absorber elements, the at least two plate holding elements being connected to each other by cross beams running along an end face with respect to at least one of a longitudinal and transverse extent of the absorber elements, wherein the absorber elements include recesses corresponding to the profile of the cross beams on the end face, into which recesses the cross beams are at least partially lowered.

18. A scattered radiation collimator comprising:
   a multiplicity of absorber elements connected one behind another in a collimation direction; and
   at least two plate holding elements, arranged substantially parallel with respect to one another and including absorber element holders for holding the absorber elements, the at least two plate holding elements being connected to each other by cross beams running along an end face with respect to at least one of a longitudinal and transverse extent of the absorber elements, wherein the at least two plate holding elements and the cross beams are arranged and designed such that an attenuation of the radiation in a radiation transit direction, caused by the at least two plate holding elements and the cross beams, in a region of the cross beams, is approximately equal to an attenuation of the radiation in the radiation transit direction, caused by the holding elements only, in a cross-beam-free region.

19. A scattered radiation collimator comprising:

a multiplicity of absorber elements connected one behind another in a collimation direction; and at least two plate holding elements, arranged substantially parallel with respect to one another and including absorber element holders for holding the absorber elements, the at least two plate holding elements being connected to each other by cross beams running along an end face with respect to at least one of a longitudinal and transverse extent of the absorber elements, wherein the absorber elements include recesses corresponding to the profile of the cross beams on the end face, into which recesses the cross beams are at least partially lowered, avoiding mechanical contact with the absorber elements.

* * * * *